US005789168A

United States Patent [19]
Leushner et al.

[11] Patent Number: 5,789,168
[45] Date of Patent: Aug. 4, 1998

[54] METHOD FOR AMPLIFICATION AND SEQUENCING OF NUCLEIC ACID POLYMERS

[75] Inventors: James Leushner, North York; May Hui, Toronto; James M. Dunn, Scarborough, all of Canada; Marina T. Larson, Yorktown, N.Y.

[73] Assignee: Visible Genetics Inc., Toronto, Canada

[21] Appl. No.: 640,672

[22] Filed: May 1, 1996

[51] Int. Cl.$^6$ ............................. C12Q 1/68; C12P 19/34
[52] U.S. Cl. ................................. 435/6; 435/91.2
[58] Field of Search .................. 435/6, 7.1, 7.5, 435/91.1, 91.2, 91.5; 436/94; 935/76, 77

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,729,947 | 3/1988 | Middendorf et al. | 435/6 |
| 4,795,699 | 1/1989 | Tabor et al. | 435/5 |
| 4,889,818 | 12/1989 | Gelfand et al. | 435/194 |
| 4,965,188 | 10/1990 | Mullis et al. | 435/6 |
| 5,079,352 | 1/1992 | Gelfand et al. | 536/23.2 |
| 5,171,534 | 12/1992 | Smith et al. | 204/612 |
| 5,352,600 | 10/1994 | Gelfand et al. | 435/194 |
| 5,427,911 | 6/1995 | Ruano | 435/6 |
| 5,484,701 | 1/1996 | Cocuzza et al. | 435/6 |

FOREIGN PATENT DOCUMENTS

| | | |
|---|---|---|
| 0265293 | 4/1988 | European Pat. Off. |
| 0386859 | 9/1990 | European Pat. Off. |
| 0655506 | 5/1995 | European Pat. Off. |
| 8907149 | 8/1989 | WIPO |
| 9302212 | 2/1993 | WIPO |
| 9308305 | 4/1993 | WIPO |
| 9426894 | 11/1994 | WIPO |
| 9601908 | 1/1996 | WIPO |
| 9601909 | 1/1996 | WIPO |

OTHER PUBLICATIONS

Innis et al. Proc. Natl. Acad. Sci. USA 85: 9436–9440, Dec. 1988.
Mason. BioTechniques 12:60–62, Jan. 1992.
Reynolds et al. BioTechniques 15: 462–467, Mar. 1993.
Ruano et al. Proc. Natl. Acad. Sci. USA 88: 2815–2819, Apr. 1991.
Xu et al. Mutation Res. 288:237–248, 1993.
Deng et al., "Simultaneous amplification and sequencing of genomic DNA (SAS): sequencing of 16S rRNA genes using total genmic DNA from *Butyrovibrio fibrisolvens*, and detection and genotyping of non–cultruable mycoplasma–like organisms directly from total DNA isolated from infected plants", *J. Microbiol. Methods* 17: 103–113 (1993).
Rao, V. B., "Direct–Sequencing of Polymerase Chain Reaction–Amplified DNA", *Anal Biochem,* 216: 1–14 (1994).
Kretz et al., "Cycle Sequencing" in *PCR Methods and Applications* 3: S107–S112 (1994).

Tabor et al., "A single residue in DNA Polymerases of the *Escherichia coli* DNA polymerase I family is critical for distinguishing between deoxy and dideoxynucleotides", *Proc. Nat'l Acad. Sci. USA.*92: 6339–6343 (1995).
Reeve et al., A novel thermostable polymerase for DNA sequencing *Nature* 376: 796–797 (1995).
Kambara et al, "Real Time Automated Simultaneous Doule Stranded DNA Sequencing Using Two–Color Fluorophore Labeling" *Biotechnology* 9: 648–651 (1991).
Sarkar et al., "Dideoxy Fingerprinting (ddF): A rapid and Efficient Screen for the Presence of Mutations" *Genomics* 13: 441–443 (1992).
Wiemann et al., "Simultaneous On–Line Sequencing on Both Strands with Two–Fluorescent Dyes" *Anal. Biochem.* 224: 117–121 (1995).
Gyllenstein et al., "Generation of single–stranded DNA by polymerase chain reaction and its application to direct sequencing of the HLA–DQA locus" *Proc. Nat'l Acad. Sci. USA* 85: 7652–7656 (1988).
Mullis et al., "Specific Synthesis of DNA in Vitro via a Polymerase–Catalyzed Chain Reaction" *Meth. Enzymol.* 155: 335–350 (1987).
Ruano et al., "Genotyping and haplotyping of polymorphisms directly from genomic DNA via coupled amplification and sequencing (CAS)" *Nucl. Acids Res.* 19: 6877–6882 (1991).
Murakawa et al., :Direct Detection of HIV–1 RNA from AIDS and ARC Patient Samples *DNA* 7: 287–295 (1988).
Carothers et al., "Point Mutation Analysis in A Mammalian Gene: Rapid Preparation of Total RNA, PCR Amplification of cDNA, and Taq Sequencing by a Novel Method" *Bio-Techniques* 7: 494–498 (1989).
Murray, V., "Improved Double–Stranded DNA Sequencing Using the Linear Polymerase Chain Reaction", *Nucl. Acids Res.* 17: 8889 (1989).
Sanger et al., "DNA Sequencing with Chain–Terminating Inhibitors", *Proc. Nat'l Acad. Sci.* 74: 5463–5467 (1977).
Miller et al., "Chain Terminator Sequencing of Double–Stranded DNA With Built in Error Correction", General Atomics Pre–Print (1991).

*Primary Examiner*—George C. Elliott
*Assistant Examiner*—Thomas G. Larson
*Attorney, Agent, or Firm*—Oppedahl & Larson

[57] ABSTRACT

Amplification and sequencing of a selected region of a target nucleic acid polymer are be performed in a single vessel. The sample is added to an amplification mixture containing a thermally stable polymerase and nucleoside feedstocks. Chain terminating dideoxynucleosides are added either at the beginning of the amplification reaction or during the course of the amplification. A thermally stable polymerase which incorporates dideoxynucleotides into an extending oligonucleotide at a rate which is no less than about 0.4 times the rate of incorporation of deoxynucleosides can be used in the amplification mixture or added with the chain terminating nucleoside.

8 Claims, 6 Drawing Sheets

AMPLIFICATION MIXTURE + SAMPLE

Amplify for Initial Cycles

ADD CHAIN-TERMINATING NUCLEOTIDE

Thermal Cycles to Extend Sequencing Primer

PRODUCT FOR LOADING ON GEL

AMPLIFICATION MIXTURE + CHAIN-TERMINATING NUCLEOTIDE + SAMPLE

Thermal Cycles to Amplify and Extend Sequencing Primer

PRODUCT FOR LOADING ON GEL

SEQUENCE LISTING ( 1 ) GENERAL INFORMATION:

( i i i ) NUMBER OF SEQUENCES: 20

( 2 ) INFORMATION FOR SEQ ID NO: 1:

( i ) SEQUENCE CHARACTERISTICS:
        ( A ) LENGTH: 22
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR1 alleles of HLA Class II genes ( x i ) SEQUENCE DESCRIPTION: SEQ ID NO:1:

TTGTGGCAGC TTAAGTTTGA AT 22

( 2 ) INFORMATION FOR SEQ ID NO: 2:

( i ) SEQUENCE CHARACTERISTICS:
        ( A ) LENGTH: 18
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR1 alleles of HLA Class II genes ( x i ) SEQUENCE DESCRIPTION: SEQ ID NO:2:

CCGCCTCTGC TCCAGGAG 18

( 2 ) INFORMATION FOR SEQ ID NO: 3:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no (iv) ANTI-SENSE: no (v) FRAGMENT TYPE: internal (vi) ORIGINAL SOURCE:
    (A) ORGANISM: human (ix) FEATURE:
    (D) OTHER INFORMATION: amplification primer for DR1 alleles of HLA Class II genes (xi) SEQUENCE DESCRIPTION: SEQ ID NO:3:

CCCGCTCGTC TTCCAGGAT      19

(2) INFORMATION FOR SEQ ID NO: 4:

(i) SEQUENCE CHARACTERISTICS:
        (A) LENGTH: 19
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for DR2 alleles of HLA Class II genes (xi) SEQUENCE DESCRIPTION: SEQ ID NO:4:

TCCTGTGGCA GCCTAAGAG      19

(2) INFORMATION FOR SEQ ID NO: 5:

(i) SEQUENCE CHARACTERISTICS:
        (A) LENGTH: 18
        (B) TYPE: nucleic acid
        (C) STRANDEDNESS: double
        (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for DR2 alleles of HLA Class II genes (xi) SEQUENCE DESCRIPTION: SEQ ID NO:5:

CCGCGCCTGC TCCAGGAT      18

(2) INFORMATION FOR SEQ ID NO: 6:

(i) SEQUENCE CHARACTERISTICS:
        (A) LENGTH: 19
        (B) TYPE: nucleic acid
        (C) STRANDEDNESS: double
        (D) TOPOLOGY: linear (i i) MOLECULE TYPE: other nucleic acid (i i i) HYPOTHETICAL: no (i v) ANTI-SENSE: no (v) FRAGMENT TYPE: internal (v i) ORIGINAL SOURCE:
    (A) ORGANISM: human (i x) FEATURE:
    (D) OTHER INFORMATION: amplification primer for DR2 alleles of
    HLA Class II genes (x i) SEQUENCE DESCRIPTION: SEQ ID NO:6:

AGGTGTCCAC CGCGCGGCG 19

(2) INFORMATION FOR SEQ ID NO: 7:

(i) SEQUENCE CHARACTERISTICS:
    (A) LENGTH: 22
    (B) TYPE: nucleic acid
    (C) STRANDEDNESS: double
    (D) TOPOLOGY: linear (i i) MOLECULE TYPE: other nucleic acid (i i i) HYPOTHETICAL: no (i v) ANTI-SENSE: yes (v) FRAGMENT TYPE: internal (v i) ORIGINAL SOURCE:
    (A) ORGANISM: human (i x) FEATURE:
    (D) OTHER INFORMATION: amplification primer for DR3, 8, 11,
    12, 13, 14 alleles of HLA Class II genes (x i) SEQUENCE DESCRIPTION: SEQ ID NO:7:

CACGTTTCTT GGAGTACTCT AC 22

(2) INFORMATION FOR SEQ ID NO: 8:

(i) SEQUENCE CHARACTERISTICS:
    (A) LENGTH: 20
    (B) TYPE: nucleic acid
    (C) STRANDEDNESS: double
    (D) TOPOLOGY: linear (i i) MOLECULE TYPE: other nucleic acid (i i i) HYPOTHETICAL: no (i v) ANTI-SENSE: no (v) FRAGMENT TYPE: internal (v i) ORIGINAL SOURCE:
    (A) ORGANISM: human (i x) FEATURE:
    (D) OTHER INFORMATION: amplification primer for DR3, 8, 11,
    12, 13, 14 alleles of HLA Class II genes (x i) SEQUENCE DESCRIPTION: SEQ ID NO:8:

CCGCTGCACT GTGAAGCTCT 20

(2) INFORMATION FOR SEQ ID NO: 9:

(i) SEQUENCE CHARACTERISTICS:

(A) LENGTH: 22
(B) TYPE: nucleic acid
(C) STRANDEDNESS: double
(D) TOPOLOGY: linear (ii) MOLECULE TYPE: other nucleic acid (iii) HYPOTHETICAL: no (iv) ANTI-SENSE: yes (v) FRAGMENT TYPE: internal (vi) ORIGINAL SOURCE:
    (A) ORGANISM: human (ix) FEATURE:
    (D) OTHER INFORMATION: amplification primer for DR4 alleles of
        HLA Class II genes (xi) SEQUENCE DESCRIPTION: SEQ ID NO:9:

GTTTCTTGGA GCAGGTTAAA CA    22

(2) INFORMATION FOR SEQ ID NO: 10:

(i) SEQUENCE CHARACTERISTICS:
    (A) LENGTH: 20
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
    (A) ORGANISM: human (ix) FEATURE:
    (D) OTHER INFORMATION: amplification primer for DR4 alleles of
        HLA Class II genes (xi) SEQUENCE DESCRIPTION: SEQ ID NO:10:

CTGCACTGTG AAGCTCTCAC    20

(2) INFORMATION FOR SEQ ID NO: 11:

(i) SEQUENCE CHARACTERISTICS:
    (A) LENGTH: 20
    (B) TYPE: nucleic acid
    (C) STRANDEDNESS: double
    (D) TOPOLOGY: linear (ii) MOLECULE TYPE: other nucleic acid (iii) HYPOTHETICAL: no (iv) ANTI-SENSE: no (v) FRAGMENT TYPE: internal (vi) ORIGINAL SOURCE:
    (A) ORGANISM: human (ix) FEATURE:
    (D) OTHER INFORMATION: amplification primer for DR4 alleles of
        HLA Class II genes (xi) SEQUENCE DESCRIPTION: SEQ ID NO:11:

CTGCACTGTG AAGCTCTCCA    20

( 2 ) INFORMATION FOR SEQ ID NO: 12:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR7 alleles of HLA Class II genes ( x i ) SEQUENCE DESCRIPTION: SEQ ID NO:12:

```
CCTGTGGCAG GGTAAGTATA                                          20
```

( 2 ) INFORMATION FOR SEQ ID NO: 13:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR7 alleles of HLA Class II genes ( x i ) SEQUENCE DESCRIPTION: SEQ ID NO:13:

```
CCCGTAGTTG TGTCTGCACA C                                        21
```

( 2 ) INFORMATION FOR SEQ ID NO: 14:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR9 alleles of HLA Class II genes ( x i ) SEQUENCE DESCRIPTION: SEQ ID NO:14:

GTTTCTTGAA GCAGGATAAG TTT                                                                23

( 2 ) INFORMATION FOR SEQ ID NO: 15:

( i ) SEQUENCE CHARACTERISTICS:
        ( A ) LENGTH: 21
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR9 alleles of
            HLA Class II genes ( x i ) SEQUENCE DESCRIPTION: SEQ ID NO:15:

CCCGTAGTTG TGTCTGCACA C                                                                  21

( 2 ) INFORMATION FOR SEQ ID NO: 16:

( i ) SEQUENCE CHARACTERISTICS:
        ( A ) LENGTH: 19
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
        ( A ) ORGANISM: human ( i x ) FEATURE:
        ( D ) OTHER INFORMATION: amplification primer for DR10 alleles
            of HLA Class II genes ( x i ) SEQUENCE DESCRIPTION: SEQ ID NO:16:

CGGTTGCTGG AAAGACGCG                                                                     19

( 2 ) INFORMATION FOR SEQ ID NO: 17:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal ( v i ) ORIGINAL SOURCE:
        ( A ) ORGANISM: human ( i x ) FEATURE:
 ( D ) OTHER INFORMATION: amplification primer for DR10 alleles
  of HLA Class II genes ( x i ) SEQUENCE DESCRIPTION: SEQ ID NO:17:

CTGCACTGTG AAGCTCTCAC                                   20

( 2 ) INFORMATION FOR SEQ ID NO: 18:

( i ) SEQUENCE CHARACTERISTICS:
  ( A ) LENGTH: 17
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
  ( A ) ORGANISM: human ( i x ) FEATURE:
  ( D ) OTHER INFORMATION: sequencing primer for DR alleles of HLA
   Class II genes ( x i ) SEQUENCE DESCRIPTION: SEQ ID NO:18:

GAGTGTCATT TCTTCAA                                      17

( 2 ) INFORMATION FOR SEQ ID NO: 19:

( i ) SEQUENCE CHARACTERISTICS:
  ( A ) LENGTH: 20
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL:no ( i v ) ANTI-SENSE: yes ( v ) FRAGMENT TYPE: internal ( v i ) ORIGINAL SOURCE:
  ( A ) ORGANISM: human ( i x ) FEATURE:
  ( D ) OTHER INFORMATION: amplification primer for HLA Class I C
   exon 2

( x i ) SEQUENCE DESCRIPTION: SEQ ID NO:19:

AGCGAGTGCC CGCCCGGCGA                                   20

( 2 ) INFORMATION FOR SEQ ID NO: 20:

( i ) SEQUENCE CHARACTERISTICS:
  ( A ) LENGTH: 25
  ( B ) TYPE: nucleic acid
  ( C ) STRANDEDNESS: double
  ( D ) TOPOLOGY: linear ( i i ) MOLECULE TYPE: other nucleic acid ( i i i ) HYPOTHETICAL:no ( i v ) ANTI-SENSE: no ( v ) FRAGMENT TYPE: internal (  v  i  ) ORIGINAL SOURCE:
    ( A ) ORGANISM: human (  i  x  ) FEATURE:
    ( D ) OTHER INFORMATION:amplification of the HLA Class I C
           exon 2

(  x  i  ) SEQUENCE DESCRIPTION: SEQ ID NO:20:

ACCTGGCCCG TCCGTGGGGG ATGAG    2 5

METHOD FOR AMPLIFICATION AND SEQUENCING OF NUCLEIC ACID POLYMERS

BACKGROUND OF THE INVENTION

This application relates to DNA sequencing reactions, and in particular to improved sequencing reaction protocols making use of thermally stable polymerase enzymes having enhanced capacity to incorporate chain terminating nucleosides during chain termination sequencing reactions.

DNA sequencing is generally performed using techniques based on the "chain termination" method described by Sanger et al., *Proc. Nat'l Acad. Sci. (USA)* 74(12): 5463–5467 (1977). Basically, in this process, DNA to be tested is isolated, rendered single stranded, and placed into four vessels. In each vessel are the necessary components to replicate the DNA strand, i.e., a template-dependant DNA polymerase, a short primer molecule complementary to a known region of the DNA to be sequenced, and individual nucleotide triphosphates in a buffer conducive to hybridization between the primer and the DNA to be sequenced and chain extension of the hybridized primer. In addition, each vessel contains a small quantity of one type of dideoxynucleotide triphosphate, e.g. dideoxyadenosine triphosphate (ddA).

In each vessel, each piece of the isolated DNA is hybridized with a primer. The primers are then extended, one base at a time to form a new nucleic acid polymer complementary to the isolated pieces of DNA. When a dideoxynucleotide is incorporated into the extending polymer, this terminates the polymer strand and prevents it from being further extended. Accordingly, in each vessel, a set of extended polymers of specific lengths are formed which are indicative of the positions of the nucleotide corresponding to the dideoxynucleic acid in that vessel. These sets of polymers are then evaluated using gel electrophoresis to determine the sequence.

Improvements to the original technique described by Sanger et al. have included improvements to the enzyme used to extend the primer chain. For example, Tabor et al. have described enzymes such as T7 DNA polymerase which have increased processivity, and increased levels of incorporation of dideoxynucleotides. (See U.S. Pat. No. 4,795,699 and EP-A1-0 655 506, which are incorporated herein by reference). More recently, Reeve et al. have described a thermostable enzyme preparation, called Thermo Sequenase™, with many of the properties of T7 DNA polymerase. *Nature* 376: 796–797 (1995). The literature supplied with the Thermo Sequenase™ product suggests dividing a DNA sample containing 0.5–2 µg of single stranded DNA (or 0.5 to 5 µg of double stranded DNA) into four aliquots, and combining each aliquot with the Thermo Sequenase™ enzyme preparation, one dideoxynucleotide termination mixture containing on ddNTP and all four dNTP's; and a dye-labeled primer which will hybridize to the DNA to be sequenced. The mixture is placed in a thermocycler and run for 20–30 cycles of annealing, extension and denaturation to produce measurable amounts of dye-labeled extension products of varying lengths which are then evaluated by gel electrophoresis.

Each of the processes known for determining the sequence of DNA can be preceded by amplification of a selected portion of the genetic material in a sample to enrich the concentration of a region of interest relative to other DNA. For example, it is possible to amplify a selected portion of a gene using a polymerase chain reaction (PCR) as described in U.S. Pat. Nos. 4,683,194, 4,683,195 and 4,683,202, which are incorporated herein by reference. This process involves the use of pairs of primers, one for each strand of the duplex DNA, that will hybridize at a site located near a region of interest in a gene. Chain extension polymerization (without a chain terminating nucleotide) is then carried out in repetitive cycles to increase the number of copies of the region of interest many times. The amplified oligonucleotides are then separated from the reaction mixture and used as the starting sample for the sequencing reaction. Gelfand et al. have described a thermostable enzyme, "Taq polymerase," derived from the organism *Thermus aquaticus*, which is useful in this amplification process. (See U.S. Pat. Nos. 5,352,600 and 5,079,352 which are incorporated herein by reference)

While the methods now available for DNA sequencing produce useful results, they all involve multiple steps. This makes them reasonably well-suited for use in a research environment, where the sequence of genetic materials is being determined for the first time, but less well-suited for use in a routine diagnostic procedure where the sequence of the same region of DNA is determined over and over again in multiple patients. For this latter purpose, it would be desirable to have a process for the sequencing of genetic materials which could be performed with fewer steps and in a single vessel, and which is therefore more suited to automation. It is the object of the present invention to provide such a method.

SUMMARY OF THE INVENTION

In accordance with one embodiment of the present invention, this and other objects are achieved using a method for amplification and sequencing of a selected region of a target nucleic acid polymer in a sample, comprising the steps of:

(a) combining the sample with first and second primers and a thermally stable polymerase enzyme which incorporates dideoxynucleosides into an extending oligonucleotide at a rate which is no less than about 0.4 times the rate of incorporation of deoxynucleosides in an amplification mixture for a plurality of amplification cycles to form a reaction mixture, said first and second primers binding to the sense and antisense strands, respectively, of the target nucleic acid polymer for amplification of the selected region;

(b) exposing the reaction mixture to a first plurality of temperature cycles each of which includes at least a high temperature denaturation phase and a lower temperature extension phase, thereby amplifying the selected region of the target nucleic acid polymer;

(c) adding a chain-terminating nucleoside to the amplified reaction mixture to form a sequencing mixture;

(d) exposing the sequencing mixture to at least one additional temperature cycle including at least a high temperature denaturation phase and a lower temperature extension phase, wherein both amplification and chain termination occur during at least the first additional temperature cycle; and (e) evaluating terminated fragments produced during the additional cycles to determine the sequence of the selected region. Alternatively, the chain terminating nucleoside may be included during all of the amplification cycles.

DETAILED DESCRIPTION OF THE INVENTION

The method of the invention utilizes the properties of enzymes like Thermo Sequenase™, namely the ability to incorporate dideoxynucleosides into an extending oligonucleotide at a rate which is no less than about 0.4 times the rate of incorporation of deoxynucleosides, to provide a combined method for the amplification and sequencing of a nucleic acid polymer from a sample. The combined method can be carried out using a single set of reagents in a single vessel. Thus, the method of the invention is ideally suited for automation.

Figure 1:
FIG. 1 illustrates a first embodiment of the present invention.
Figure 1:

FIG. 1 illustrates a first embodiment of the present invention. As shown in FIG. 1, a sample containing a target nucleic acid polymer which is to be amplified and sequenced is combined with an amplification mixture containing two primers, a mixture of dNTP's and thermostable polyermase in a buffer suitable for amplification. The mixture is amplified through an initial set of cycles, for example 15-20 cycles. At this stage reagents for forming chain termination products, namely a dideoxynucleotide (ddNTP) and optionally additional thermostable polymerase, dNTP's and a labeled sequencing primer are added and additional cycles (for example another 15-20 cycles) are performed during which both amplification and the formation of chain termination products occurs. At the end of these cycles, the product mixture is evaluated to determine the lengths of the chain termination products, and hence the positions of the particular base corresponding to the ddNTP within the target nucleic acid polymer.

Within the scope of this general method, there are a number of variations which are possible. For example, it is possible to use one of the amplification primers as the sequencing primer, thus obviating the need to add additional sequencing primer at the time the ddNTP is added. In this case, one of the amplification primers is advantageously labeled with a detectable label, for example a fluorescent label, for use in the subsequent detection of the chain termination products.

Another variation which may be advantageous is the use of asymmetric amplification to preferentially amplify one strand of the target nucleic acid. In this case, the primer which will produce the desired sequencing template strand is combined with the sample in an amount greater than the other primer, e.g., a 10 to 50-fold excess. More amplification cycles may be required to take full advantage of asymmetric amplification.

It may also be advantageous to biotinylate one of the primers during amplification. When this is done, a partial separation of reagents can be accomplished prior to the introduction of the sequencing reagents by capturing the biotinylated amplification products on an avidin or streptavidin-coated support, separating the liquid medium from the support and replacing the liquid medium with the sequencing reagents. In a preferred use of this approach, the biotinylated products are captured on magnetic beads, which are precipitated with a magnet to facilitate separation of the amplification liquid. While this step is not necessary to the method, and is not intended to accomplish complete removal of the amplification reagents, the use of this step can improve the sensitivity of the procedure by reducing the number of background oligonucleotides, particularly where a separate labeled-sequencing primer is added with the ddNTP.

Figure 2:
FIG. 2 illustrates a second embodiment of the present invention.

FIG. 2 shows a second embodiment of the invention schematically. In this embodiment, a ddNTP is included from the beginning of the amplification/sequencing procedure. Amplification and the formation of chain-terminated products proceeds simultaneously, with the relative ratio of products depending on the concentration of the ddNTP relative to the corresponding dNTP and the relative rate of incorporation of the ddNTP compared to dNTP of the polymerase enzyme used.

The operation of this embodiment can be understood in the context of a hypothetical 200 nt DNA fragment having equal amounts of each base. This means that there will be 50 potential truncation events during the cycle. For each cycle, some of the amplification products would be full length (and thus subject to further amplification) and some would be truncated at the points where the ddNTP was added. If each of these truncation events has a statistical likelihood of occurring 1 time in 500 as a result of the relative concentration of ddNTP compared to dNTP and the relative incorporation by the enzyme, then overall a truncation product will occur in slightly less than ten percent of the reactions. In Table 1, shows the relative amounts of amplified and chain-termination products formed after 10, 20 and 30 cycles of simultaneous amplification and chain-termination reaction of this 200 nt oligonucleotide assuming various ratios of truncated to amplified product.

TABLE 1

| Cycles | truncation ratio = 0.1 | | truncation ratio = 0.3 | | truncation ration = 0.5 | |
| --- | --- | --- | --- | --- | --- | --- |
| | truncated | amplified | truncated | ampli-fied | trun-cated | ampli-fied |
| 10 | 32 | 613 | 86 | 202 | 57 | 57 |
| 20 | 41,000 | 376,000 | 17,400 | 40,462 | 3,300 | 3,300 |
| 30 | 25.6×10$^6$ | 230×10$^6$ | 3.5×10$^6$ | 8.2×10$^6$ | 190,000 | 190,000 |

Rather anomalously, lower truncation ratios (that is less truncation) results in the formation of more truncation product. Lower truncations rates also lead to a higher level of amplified products relative to truncation products, however. Thus, it may be preferred to conduct the reaction under conditions of concentration and enzyme selectivity which combine to give a truncation ration of around 0.3, at which 30 cycles provides a significant yield of truncation products with only about a 2 to 3-fold excess of full length amplification products.

In this embodiment of the invention, a single labeled primer is used as both the amplification primer and the sequencing primer. This means that full length product will be detected during sequencing and will be a substantial band relative to any of the individual truncation products. To avoid loosing information due to the size of this band, it is advantageous to use a relatively long primer, for example a 20–25 mer such that the difference in length between the full length product and the longest possible truncation product will be 21 to 26 bases.

It may also be advantageous to label the second amplification primer with a label such as biotin that renders it readily removable from the solution by immobilization on a solid support. In this case, the amount of unlabeled oligonucleotide can be substantially reduced, thus improving the performance of the subsequent electrophoresis by adding avidin or streptavidin-coated beads to separate the other strand.

The performance of this embodiment can also be improved by the use of asymmetric amplification in which the sequencing template strand is amplified in greater amounts than the other strand. This is achieved by adding an excess, e.g. a 10–50-fold excess of the primer which initiates synthesis of the sequencing template strand. When the first stage asymmetric amplification is completed, the fluorescently-labeled sequencing primer is added. Improved results flow from the reduced competition between sequencing and the non-template strand primer for primer site hybridization.

It may also be advantageous when possible to select a primer sequence which does not include the base corresponding to the ddNTP of the sequencing reaction to avoid truncations within the primer portion of the product oligonucleotide. This means that four separate sets of amplification/sequencing primers may need to be constructed for any one region. This is less burdensome than it might seem, however, since in many cases sequencing of only a single base is sufficient for diagnostic purposes. (See U.S. patent application Ser. No. 08/577,858, which is incorporated herein by reference).

Figure 3A:
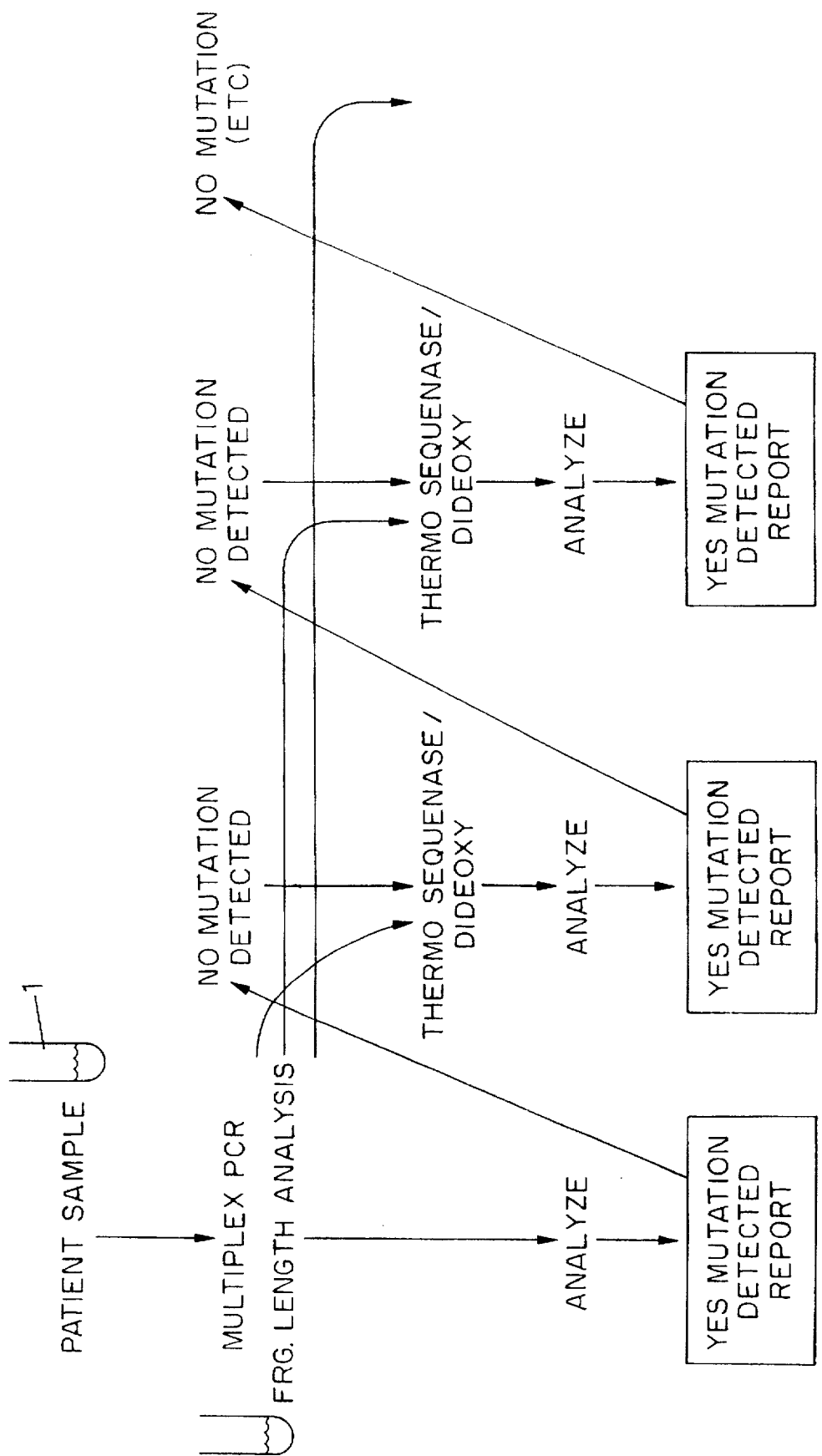
FIGS. 3A and 3B illustrate a diagnostic method which incorporates the amplification and sequencing process of the present invention with a fragment-based analysis.
Figure 3B:
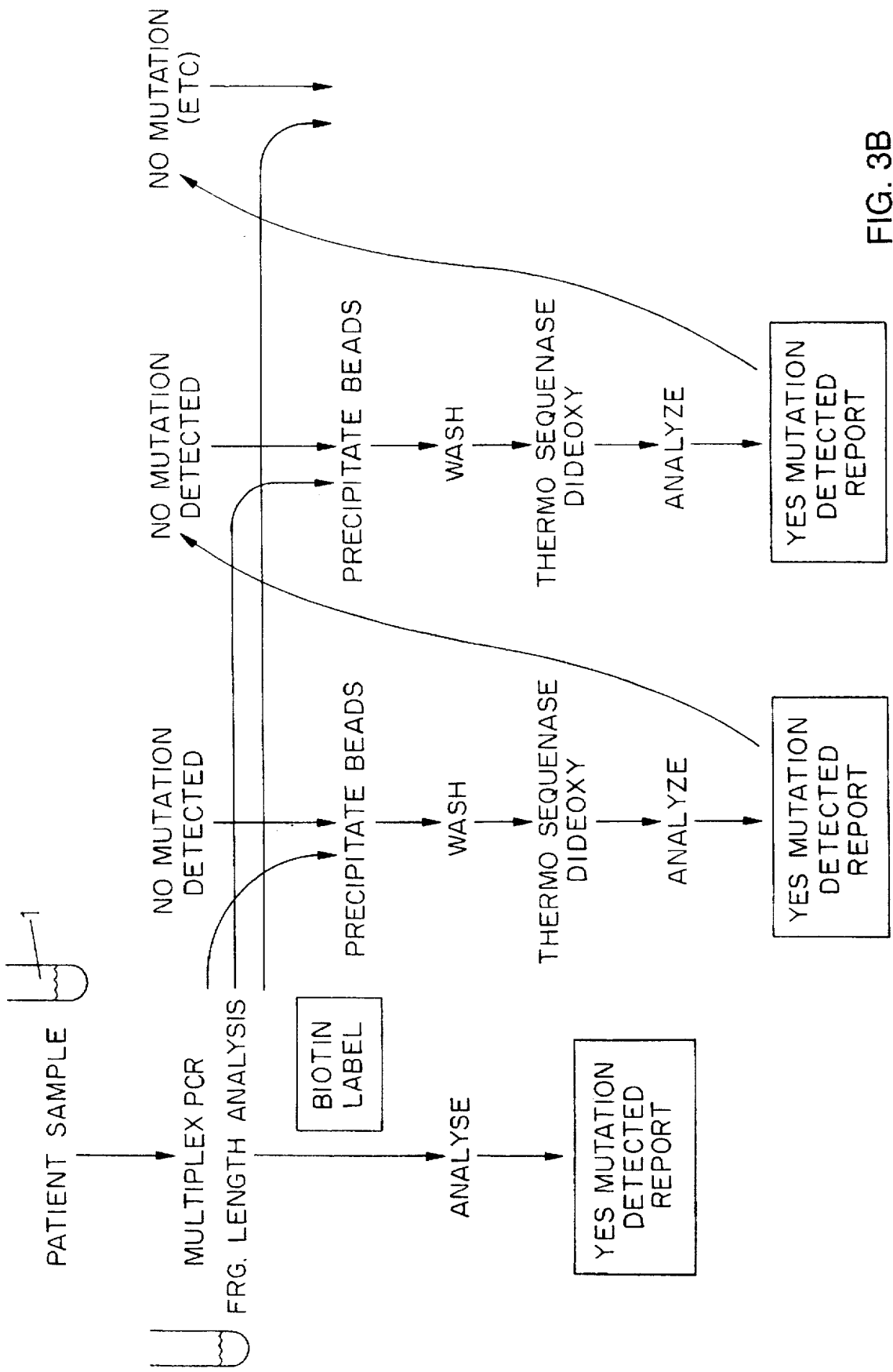
Figure 4:
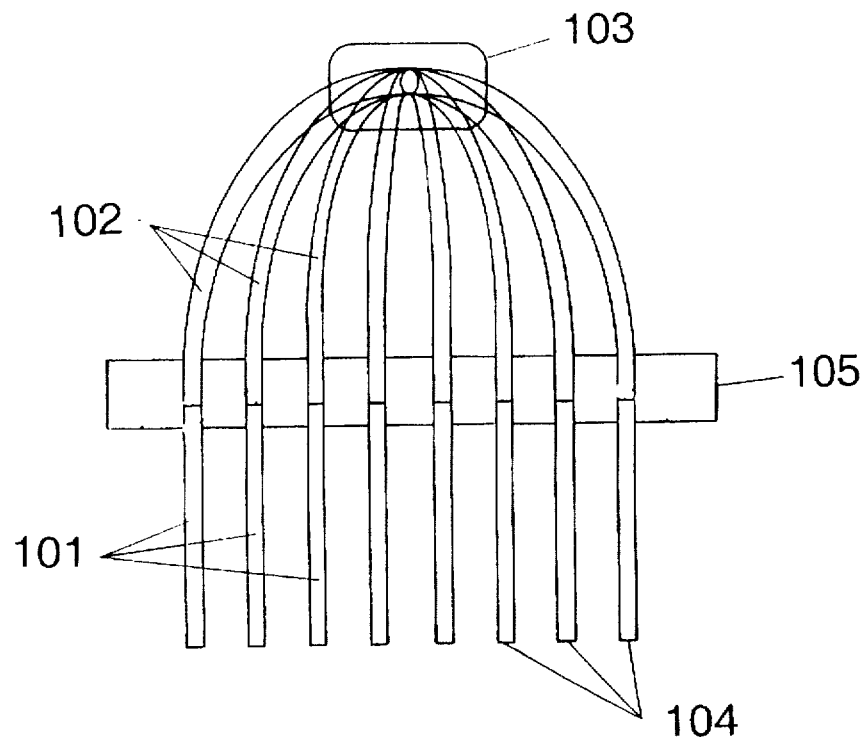
FIG. 4 depicts a portion of an apparatus useful in carrying out the present invention.

FIGS. 3A and 3B illustrates a particularly useful application of the method of the present invention as part of an overall diagnostic strategy in which a series of analytical techniques may be performed on the same sample, depending on the outcome of the initial test. Hierarchical techniques of this type are described in U.S. patent applications Ser. Nos. 08/271,942, 08/271,946, and 08/388,381 which are incorporated herein by reference.

As shown in FIGS. 3A and 3B, a patient sample 1 is first subjected to multiplex PCR to produce a complex mixture of amplification products. Since many clinically significant conditions, for example mutations in the RB1 gene, may involve deletions which are readily and inexpensively detectable by performing fragment length analysis on this mixture, a first step in many hierarchical analysis will be such a fragment length analysis.

According to the hierarchical model, if the results of the fragment length analysis fails to show a mutation, the sample 1 if further analyzed, for example by sequencing a selected exon. Prior to the present invention, however, this required the individual amplification of the selected exon from the sample because the there was not enough template in the initial multiplex PCR reaction to serve as a sequencing template. Using the method of the present invention, however, an aliquot of the original multiplex PCR amplification mixture can be used as the starting material for multiple cycles of combined amplification and sequencing. Thus, the multiplex PCR amplification mixture is combined with amplification and/or labeled sequencing primers and amplified and sequenced in a single reaction vessel. Preferably, the multiplex amplification PCR is performed using capturable primers (for example biotin-labeled primers) and separated from the multiplex amplification reagents using affinity beads (e.g. avidin-coated beads) prior to the addition of the amplification/sequencing reagents. (FIG. 3B). Additional aliquots of the multiplex reaction mixture may be processed to sequence different regions if no mutation is detected in the first sequencing step.

It should be noted that the multiplex reaction performed in the first step of this embodiment makes used of labeled primers. Fluorescence from these primers may interfere with observation of a few peaks in the sequencing ladder. This interference can be minimized by utilizing a nested sequencing primer, which produces fragments having a maximum length which is shorter than the multiplex amplification products, or by the utilization of distinguishable labels for the multiplex amplification and sequencing primers.

EXAMPLE 1

Identification of HLA Class II gene alleles present in an individual patient sample can be performed using the method of the instant invention. For example, DRB1 is a polymorphic HLA Class II gene with at least 107 known alleles (See Bodmer et al. Nomenclature for Factors of the HLA System, 1994. Hum. Imm. 41, 1–20 (1994)).

The broad serological subtype of the patient sample DRB1 allele is first determined by attempting to amplify the allele using group specific primers.

Genomic DNA is prepared from the patient sample using a standard technique such as proteinase K proteolysis. Allele amplification is carried out in Class II PCR buffer:

10 mM Tris pH 8.4
50 mM KCl
1.5 mM MgCl2
0.1% gelatin
200 microM each of dATP, dCTP, dGTP and dTTP
12 pmol of each group specific primer
40 ng patient sample genomic DNA Groups are amplified separately. The group specific primers employed are:

|  |  |  | PRODUCT SIZE |
|---|---|---|---|
| DR 1 | | | |
| 5'-PRIMER: | TTGTGGCAGCTTAAGTTTGAAT | [Seq ID No. 1] | 195&196 |
| 3'-PRIMERS: | CCGCCTCTGCTCCAGGAG | [Seq ID No. 2] | |
| | CCCGCTCGTCTTCCAGGAT | [Seq ID No. 3] | |
| DR2, 15 and 16 | | | |
| 5'-PRIMER: | TCCTGTGGCAGCCTAAGAG | [Seq ID No. 4] | 197&213 |
| 3'-PRIMERS: | CCGCGCCTGCTCCAGGAT | [Seq ID No. 5] | |
| | AGGTGTCCACCGCGCGGCG | [Seq ID No. 6] | |

-continued

| | | | PRODUCT SIZE |
|---|---|---|---|
| DR3, 8, 11, 12, 13, 14 | | | |
| 5'-PRIMER: | CACGTTTCTTGGAGTACTCTAC | [Seq ID No. 7] | 270 |
| 3'-PRIMER: | CCGCTGCACTGTGAAGCTCT | [Seq ID No. 8] | |
| DR4 | | | |
| 5'-PRIMER: | GTTTCTTGGAGCAGGTTAAACA | [Seq ID No. 9] | 260 |
| 3'-PRIMERS: | CTGCACTGTGAAGCTCTCAC | [Seq ID No. 10] | |
| | CTGCACTGTGAAGCTCTCCA | [Seq ID No. 11] | |
| DR7 | | | |
| 5'-PRIMER: | CCTGTGGCAGGGTAAGTATA | [Seq ID No. 12] | 232 |
| 3'-PRIMER: | CCCGTAGTTGTGTCTGCACAC | [Seq ID No. 13] | |
| DR9 | | | |
| 5'-PRIMER: | GTTTCTTGAAGCAGGATAAGTTT | [Seq ID No. 14] | 236 |
| 3'-PRIMER: | CCCGTAGTTGTGTCTGCACAC | [Seq ID No. 15] | |
| DR10 | | | |
| 5'-PRIMER: | CGGTTGCTGGAAAGACGCG | [Seq ID No. 16] | 204 |
| 3'-PRIMER: | CTGCACTGTGAAGCTCTCAC | [Seq ID No. 17] | |

The 5'-primers of the above groups are terminally labeled with a fluorophore such as a fluorescein dye at the 5'-end.

The reaction mixture is mixed well. 2.5 units Taq Polymerase are added and mixed immediately prior to thermocycling. The reaction tubes are placed in a Robocycler Gradient 96 (Stratagene, Inc.) and subject to thermal cycling as follows:

| 1 cycle | 94 C. 2 min |
|---|---|
| 10 cycles | 94 C. 15 sec |
| | 67 C. 1 min |
| 20 cycles | 94 C. 10 sec |
| | 61 C. 50 sec |
| | 72 C. 39 sec |
| 1 cycle | 72 C. 2 min |

4 C. cool on ice until ready for electrophoretic analysis.

Seven reactions (one for each group specific primer set) are performed. After amplification 2 microl of each of the PCR products are pooled, and mixed with 11 microl of loading buffer consisting of 100% formamide with 5 mg/ml dextran blue. The products are run on a 6% polyacrylamide electrophoresis gel in an automated fluorescence detection apparatus such as the Pharmacia A.L.F.™ (Uppsala, Sweden). Size determinations are performed based on migration distances of known size fragments. The serological group is identified by the length of the successfully amplified fragment. Only one fragment will appear if both alleles belong to the same serological group, otherwise, for heterozygotes containing alleles from two different groups, two fragments appear.

Once the serological group is determined, specificity within the group is determined by single nucleotide sequencing according to the invention of U.S. patent application Ser. No. 08/577,858.

Each positive group from above is individually amplified for sequence analysis. The PCR amplification primers are a biotinylated 3'-primer:

5' Biotin-CCGCTGCACTGTGAAGCTCT 3' [Seq ID No. 8]

and the appropriate 5'-primer described above. The conditions for amplification are identical to the method described above except that Thermo Sequenase™ is used as the polymerase, and the Thermo Sequenase™ buffer is used.

After amplification, sequencing is performed using the following sequencing primer:

5'-GAGTGTCATTTCTTCAA [Seq ID No. 18]

as follows. The PCR product (10 ul) is mixed with 10 ul of washed Dynabeads M-280 (as per manufacturers recommendations, Dynal, Oslo, Norway) and incubated for up to 1 hr at room temperature. The beads are isolated with a magent and the supernatant is removed. The beads separated beads are then washed with 50 ul of 2× BW buffer (10 mM Tris, pH 7.5, 1 mM EDTA, 2M NaCl) followed by 50 ul of 1× TE buffer (10 mM Tris, 1 mM EDTA). After washing, resuspend the beads in 10 ul of TE and take 3 ul for the sequencing reaction which consists of:

3 ul bound beads
3 ul sequencing primer (30 ng total)
2 ul 10× sequencing buffer (260 mM Tris-HCl, pH 9.5, 65 mM MgCl2)
2 ul of Thermo Sequenase™ (Amersham Life Sciences, Cleveland) (diluted 1:10 from stock, 32 units/ul)
3 ul $H_2O$
Final Volume=13 ul. Keep this sequencing reaction mix on ice.

Remove 3 ul of the sequencing reaction mix and add to 3 ul of one of the following mixtures, depending on the termination reaction desired.

A termination reaction:
250 to 750 microM each of dATP, dCTP, dGTP, and dTTP;
2.5 microM ddATP
C termination reaction:
250 to 750 microM each of dATP, dCTP, dGTP, and dTTP;
2.5 microM ddCTP
C termination reaction:
250 to 750 microM each of dATP, dCTP, dGTP, and dTTP;
2.5 microM ddGTP
T termination reaction:
250 to 750 microM each of dATP, dCTP, dGTP, and dTTP;
2.5 microM ddTTP
Total termination reaction volume: 6 ul An oil overlay is added, and the termination reaction mixture is cycled in a Robocycler™ for 25 cycles (or fewer if found to be satisfactory):

95 C. 30 sec
50 C. 10 sec
70 C. 30 sec

After cycling add 12 ul of loading buffer consisting of 100% formamide with 5 mg/ml dextran blue, and load appropriate volume to an automated DNA sequencing apparatus, such as a Pharmacia A.L.F.

EXAMPLE 2

DNA sequence for HLA Class I C exon 2 can be obtained according to the method of the invention as follows:

Asymmetric amplification of the HLA Class I C exon 2 sequencing template strand is obtained using an excess ratio (10–50 fold) of template strand primer as follows:
Primer 1: 5'-AGCGAGTGCCCGCCCGGCGA-3' [SEQ. ID. No.: 19]
Primer 2: 5'-ACCTGGCCCGTCCGTGGGGGATGAG-3' [SEQ. ID. No.: 20]
The following reactants were combined in an Eppendorf tube at 4 degrees C. in the following amounts:
Primer 1: 1 pmole
Primer 2: 20 pmole
10 mM Tris pH 8.6
1.5 mM MgCl2
5% DMSO
50 mM KCl
0.2 mM dNTPs (i.e. 0.05 of each dATP, dCTP, dGTP, dTTP)
0.25 units Taq Polymerase
Final reaction volume: 2 microliters. This small volume allowed for the reaction to proceed close to completion, and particularly to consume available dNTPs during the amplification step.

The reaction was overlaid with 10 microliters of Chill Out Liquid Wax and the tube was place in a Perkin-Elmer 9600 Thermo-Cycling apparatus. 20 thermal cycles were employed as follows:
95 C. 5 sec
64 C. 10 sec
72 C. 8 sec
After thermal cycling, the reaction vessel was cooled to 4 C. for 10 min, whereupon the Chill Out Wax solidified.

The following sequencing mix was then added on top of the solidified wax plug:
1.2 microliters (20 pmoles) of Sequencing primer:
5'-fluorescent label-GGAGGGTCGGGCGGGTCT-3' [SEQ. ID No.: 21]
1.0 microliters Amersham Thermo Sequenase sequencing buffer
1.0 microliters thermal stable polymerase (Thermo Sequenase) (3 units)
1.0 microliters 20% (v/v) DMSO
3.0 microliters 1:100 ratio of ddGTP (or other ddNTP) and 4 dNTPs (final concentrations of 2.5 microM and 250 microM respectively).

The reaction was thermal cycled at the following temperatures in a Perkin-Elmer 9600 thermal cycling apparatus for 15 cycles as follows:
95 C. 15 sec
50 C. 5 sec
70 C. 15 sec
After the thermal cycles, the reaction was cooled to 4 C. It was mixed with 6 microliters stop solution (formamide and glycerol), and 1–3 (up to 10) microliters were loaded per lane onto an automated electrophoresis/detection apparatus such as the Pharmacia A.L.F.

EXAMPLE 3

The procedure of Example 2 was repeated, except that the initial amplification phase was modified to use Thermo Sequenase® was used in place of Taq Polymerase. The following components were used in the amplification mixture:
3 ul DNA (300 ng)
3 ul primers (20 pmol:1 pmol ratio)
2 ul 10× buffer (Thermo Sequenase™ reaction buffer)
2 ul enzyme (Thermo Sequenase™)
3 ul DMSO (20% DMSO in water)
The entire 13 ul was placed in 15 ul of nucleotide mix containing 1 ul of a 10 mM mix of dATP, dCTP, dGTP and dTTP and 14 ul water The combination was thermocycled using for 39 cycles as follows:

| annealing 60 | initial time | 50 sec, extended by 1 second after each cycle |
|---|---|---|
| denaturing 94 | 30 sec | |
| extension 72 | initial time | 30 sec, extended by 2 second after each cycle |

The resulting amplicon was evaluated by electrophoresis and showed clean production of the C and B locus of the HLA C gene.

The dideoxy sequencing mixture was then added and thermocycled as described in Example 2. The result was a clean sequencing ladder for the amplified regions.

The various embodiments of the invention described above provide the ability to perform both amplification and sequencing of a sample in a single reaction vessel. As noted above, in many cases of clinical significance it may be sufficient to determine the position of just one base within a target nucleic acid polymer in the sample. In this case, the complete diagnostic process can be completed in a single vessel, thus greatly simplifying the requirements of the process for automation. When explicit determination of all four bases is considered necessary, the process can be carried out in four separate tubes, one for each sequencing reaction. These tubes may all incorporate a single dye to label the sequencing primers, in which case the products of each reaction are loaded onto a separate lane of a sequencing gel; or the tubes may each incorporate a distinct fluorescent label, in which case the sequencing reaction products may be combined prior to loading onto a multi-dye instrument.

The amplification and sequencing reactions in accordance with the invention are advantageously carried out in an apparatus designed to perform both sets of reactions (amplification and sequencing) in a single reaction vessel. A preferred type of apparatus is one which is automated to perform both the sample preparation and the thermocycling steps. FIGS. 4–7 depict an apparatus suitable for this purpose.

In the apparatus of FIGS. 4–7, a plurality of capillary tubes 101, open at both ends, are used as the reaction vessels. The capillaries 101 are held by a support 105 to permit transport as a group between a sample preparation zone 210 and a thermal cycling zone 211 within the apparatus. Capillary tube 101 is typically made of glass or another inert substance. It preferably has an inside diameter of about 1.1 mm, such as Fisherbrand™ or Pyrexbrand™ capillaries sold by Fisher Scientific (Ottawa, Canada).

The capillaries 101 are connected to a sensitive two way pump 103 either directly or by way of tubing 102. A single pump 103 may be used for all capillaries, or each capillary may have its own dedicated pump. When pump 103 is operated the open end of capillary tip 104 withdraws or expels liquid as programmed. Pump 103 is preferably a piston displacement pump with linear actuators. The motor of pump 103 must have sufficient torque to drive the linear actuator, while having sufficient sensitivity to allow precise measurements of very small liquid samples. The Drummond Nanoject™ pump (Cat No. 3-00-203-X, Drummond Scientific Co., Broomall, Pa.) is sensitive to measure nanoliters of fluid is appropriate for use in the apparatus.

The support 105 is positioned in a robotic apparatus 200 which provides X, Y, and Z displacement of the support 105 relative to sample preparation trays 201 and an integrated thermal cycling chamber 202. The position of support 105 and the associated capillaries 101 is controlled by the programming of robotic apparatus 200. A programmable controller is present, though not shown. Many types of robotic apparatus are currently employed in the art, as exemplified by the existing commercial sample preparation apparatuses. Programmable robots position capillary tip 104 in a reagent well 203 and then activate pump 103 to draw liquid into capillary 101. The robot then removes capillary tip 104 from the well and moves it to another position.

A plurality of trays 201, each of which may hold a microtiter plate or other container for holding reagents and/or samples for analysis, are disposed within the dimensional parameters of the X, Y, and Z axes of the robot, as indicated. Trays 201 are temperature controlled for preparation of reactants.

Wells 203 of microtiter plate 201 are loaded with reagents for selected thermal cycling reactions, for example: reagents for PCR amplification; reagents for DNA sequencing and stop reagents such as formamide and visible dye, used for inhibiting enzyme action. The addition of reagents to microtiter plate 201 may be done by a commercially available automated sample preparation instrument.

Figure 6:
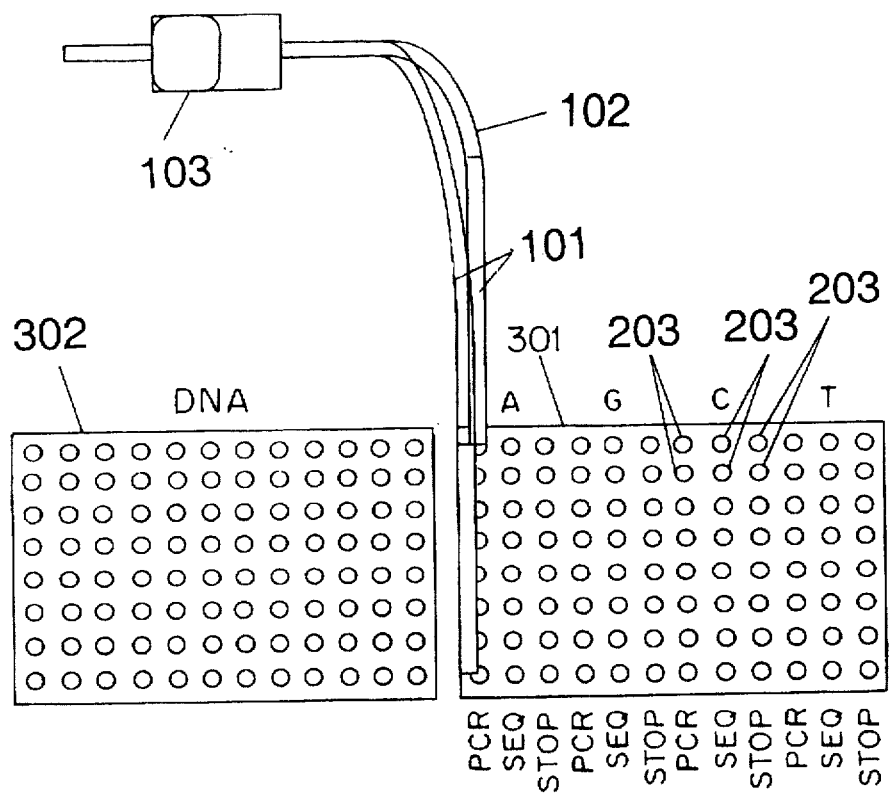
FIG. 6 depicts a portion of an apparatus useful in carrying out the present invention.
Figure 5:
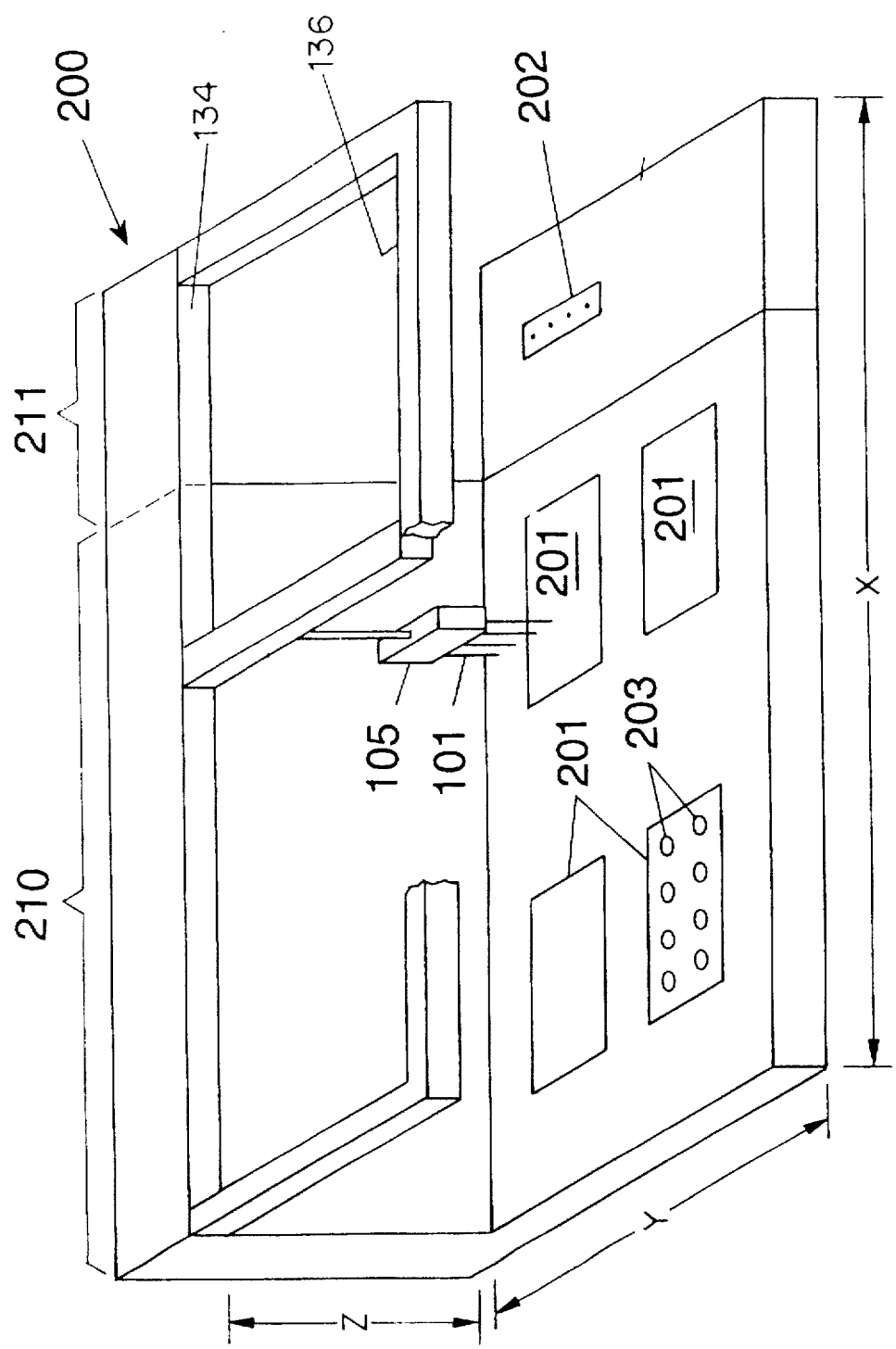
FIG. 5 depicts a robotic apparatus useful in carrying out the present invention.

Reagents are positioned in the wells 203 a fashion convenient for sequential utilization as shown in FIG. 6. Reagents for nucleic acid sample preparation are present in reagent plate 301. As shown, PCR reagent, sequencing reaction mixture and stop solution are present in alternating columns of wells 203. A separate microtiter plate 302 is loaded with sample DNA to be tested. The plate is kept at 4 degrees C. during the preparation period.

To carry out the method of the present invention, fresh capillaries 101 dips into DNA samples to be tested in microtiter plate 302. A series of 8 or 12 capillaries is most suitable for use with standard microtiter plates. Pump 103 draws an aliquot of DNA from plate 302 into the capillary 101. Capillary tip 104 is removed by the positional robot and inserted into PCR reagent wells in plate 301. These wells generally include all the reaction components required for PCR amplification of the sample DNA, although two or more wells can be used to provide the reagents for one reaction if desired.

The DNA sample is expelled into wells of plate 301 containing PCR reaction mixture and fully drawn up and down two or more times to mix. Finally, an appropriate reaction volume (e.g. 2 microliters) of mixture is drawn into capillary 101, capillary tip 104 is removed from the well and the mixture is drawn up the capillary approximately 2 cm. The positional robot then moves capillary 101 to the thermal cycling zone 211.

Within the thermocycling zone 211 of the apparatus is a thermocycling chamber 202 which contains a sealing device for reversibly sealing the capillaries 101. As shown FIG. 7, sealing mechanism 400 is provided to reversibly seal a capillary having a reaction mixture therein. Sealing mechanism 400 has a conformable sealing surface 402 against which the available open ends of a row of capillary tubes can be placed flush, thereby sealing them. Sealing surface 402 is made of a chemically inert elastic substance which must be sufficiently deformable to match the imperfections of capillary tip 104, e.g., rubber or neoprene. Sealing surface 402 is suitably sterile to prevent contamination of samples. Further, a transport system can be provided, for example in the form of a supply roll 403 and uptake roll 403', to provide a fresh sealing surface for each successive application of the capillary or capillaries.

Loaded capillary 401 is placed into thermal cycler 202, and capillary tip 104 is pressed snugly against sealing surface 402. When pressing tip 104 into sealing surface 402, the positional controller robot directs its force directly along the axis of the capillary and does not deflect from this axis, in order to limit breakage of capillaries. The sealing mechanism is preferably of small size in order to minimize the thermal mass. It is preferably located entirely within the sample compartment.

Once sealed, air pressure from the pump is increased. The air pressure in the capillary is maintained higher than the vapor pressure of the sample to prevent solution from escaping, especially during the high temperature period of the thermal cycles. The air pressure may be increased and fixed prior to the thermal cycling. Alternatively, the air pressure may be dynamic during the course of the thermal cycles and increase or decrease as preferred. Some changes of air pressure inside the reversibly sealed capillary will also result from the temperature changes during thermal cycling. Sealing surface 402, therefore, must also be sufficiently rigid to contain the increased air pressure in the capillary.

Figure 7:
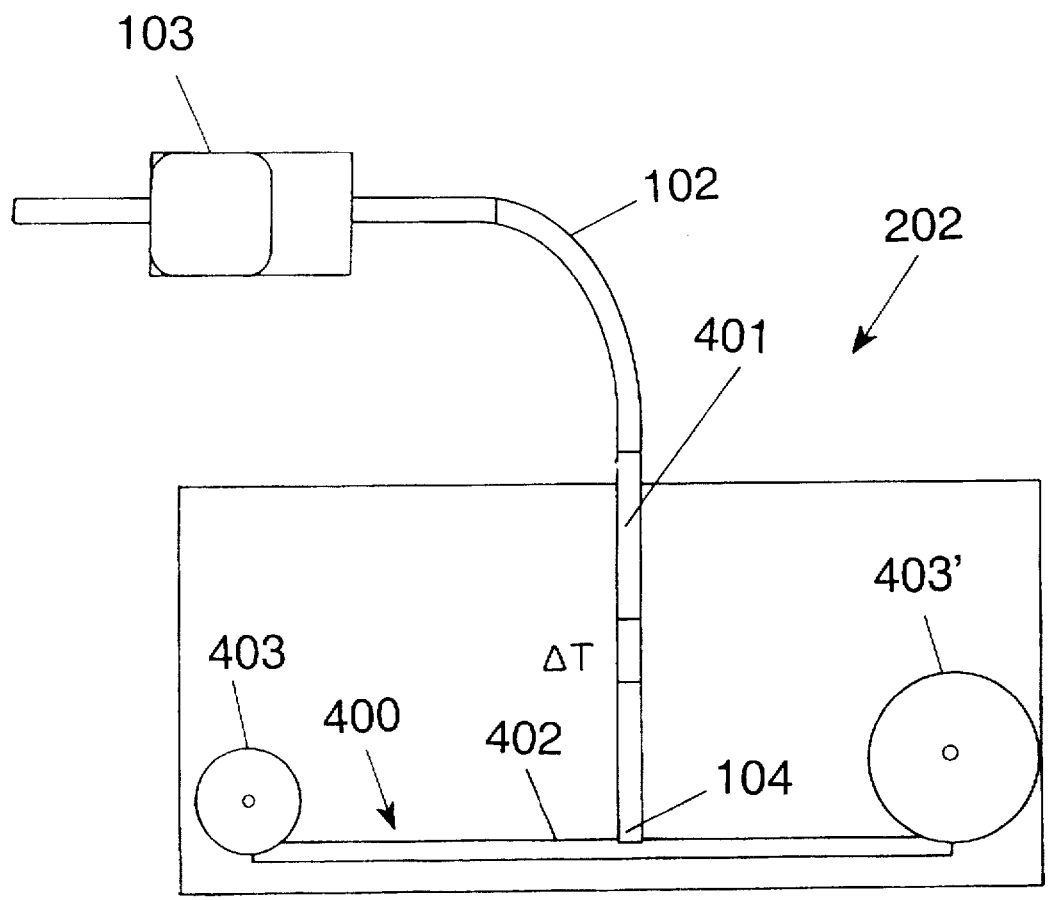
FIG. 7 depicts a side cross-sectional view of a thermocycling device having a reversible sealing mechanism useful in carrying out the present invention.

Although a single capillary 401 is depicted in FIG. 7, it is understood that a row of capillaries having reaction mixture may be treated as described. Multiple capillaries may be sealed and undergo thermal cycling by contacting them with the sealing surface at the same time.

Once sealed, capillaries are then subjected to thermal cycling by introducing successive waves of heated air or other heat conducting gas or fluid. Thermal heat cycles depend on the actual reaction, but may consist of the following. Heat to 94° for 2 minutes. Then execute 35 cycles of 94° for 30 seconds; 50° for 30 seconds; 65° for 2 minutes; then finish at 65° for 7 minutes.

After the appropriate number of thermal cycles, the reaction mixture is brought to room temperature or below and the air pressure inside the capillary is returned to standard. The air-tight seal is broken by removing the contact between the capillaries and the plug. This is automatically accomplished by the robotic arm moving the capillaries away from the plug. The capillaries are removed from the thermal cycler by means of the robotic arm and returned to the sample preparation zone 210.

After the PCR reactions, the tip 104 of each capillary 101 is placed in a sequencing reaction mixture. Each sequencing reaction mixture contains appropriate reagents for practicing the method of the invention, including one species of chain terminating dideoxynucleotide (either ddATP; ddCTP; ddGTP or ddTTP), and optionally other reaction components such as: Thermo Sequenase™ buffer (final: 26 mM Tris-HCl, pH 9.5, 6.5 mM MgCl2); ~30 ng/5 pM Fluoresceinated sequencing primer; distilled water; Thermo Sequenase™ enzyme; plus desired amounts of dNTPs as desired.

Sample is thoroughly mixed by successive drawing and expulsion from the capillaries. Finally, an appropriate reaction volume (e.g. 2 microliters) is drawn into the capillary 101; the tip 104 is removed from the sequencing reaction mixture well and the sample is drawn 2 cm up into the capillary. The capillary 101 is moved back to the thermal cycling zone 211 and the tip 104 is pressed into the sealing surface, preferably at a different location to avoid contamination from the previous reaction. Air pressure is increased inside the capillary to prevent evaporation of sample. Thermal cycling then takes place to produce sequencing fragments.

After the appropriate number of thermal cycles, the reaction products are cooled to room temperature or below; the air pressure inside the capillaries is returned to ambient; and the capillaries are then removed from the thermal cycling zone 210. At this point the sample may be mixed with stop solution and transferred for loading on an electrophoresis gel.

We claim:

1. A method for analyzing a nucleic acid-containing sample comprising the steps of:

performing a multiplex amplification reaction on the nucleic acid-containing sample using a plurality of amplification primers pairs, one pair for each of a plurality of regions to be analyzed, to produce a mixture of amplified fragments, one species of amplified fragment for each of the plurality of regions to be analyzed; and determining the sequence of at least one of the species of amplified fragments, wherein the sequence is determined by combining the mixture of amplified fragments produced in the multiplex amplification reaction directly with a sequencing reaction mixture for the production of sequencing fragments and evaluating the sequencing fragments produced therefrom.

2. The method of claim 1, wherein at least one aliquot of the mixture of amplified fragments produced in the multiplex amplification reaction is combined with a sequencing mixture comprising first and second sequencing primers, a nucleotide triphosphate feedstock mixture, a chain-terminating nucleotide triphosphate, and a thermally stable polymerase enzyme which incorporates dideoxynucleotide triphosphates into an extending nucleic acid polymer at a rate which is no less than 0.4 times the rate of incorporation of deoxynucleotide triphosphates to form a sequencing reaction mixture, said first and second sequencing primers binding to the sense and antisense strands, respectively, of the amplified fragments from a selected one of the regions; and wherein the sequencing reaction mixture is exposed to a plurality of temperature cycles each of which includes at least a high temperature denaturation phase and a lower temperature extension phase, thereby producing a plurality of terminated fragments; and that the terminated fragments are evaluated to determine the position of the base corresponding to the chain-terminating nucleotide triphosphate within the selected fragment.

3. The method according to claim 2, wherein at least one primer of each pair of amplification primers used in the multiplex amplification reaction is labeled with a capturable label, and wherein the amplified fragments are captured on a solid support and washed prior to combining them with the sequencing mixture.

4. The method according to claim 3, wherein the capturable label is biotin.

5. The method according claim 2, wherein the thermostable polymerase enzyme is THERMO SEQUENASE™.

6. The method according to claim 2, wherein at least one of the first and second sequencing primers in the sequencing mixture is labeled with a fluorescent label.

7. The method according to claim 2, wherein the first and second sequencing primers in the sequencing mixture are each labeled with a different spectroscopically-distinguishable fluorescent label.

8. The method according to claim 1, wherein the species of amplified fragments produced by the pairs of amplification primers each have a different length.

* * * * *